US008562590B2

(12) United States Patent
Yodfat et al.

(10) Patent No.: US 8,562,590 B2
(45) Date of Patent: *Oct. 22, 2013

(54) SYSTEMS AND METHODS FOR SUSTAINED MEDICAL INFUSION AND DEVICES RELATED THERETO

(75) Inventors: Ofer Yodfat, Maccabim-Reut (IL); Avi Neta, Misgav (IL); Gavriel J. Iddan, Haifa (IL)

(73) Assignee: Medingo Ltd., Yokneam (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/065,230

(22) Filed: Mar. 16, 2011

(65) Prior Publication Data

US 2011/0172603 A1 Jul. 14, 2011

Related U.S. Application Data

(63) Continuation of application No. 11/397,115, filed on Apr. 3, 2006, now Pat. No. 7,935,104.

(30) Foreign Application Priority Data

Nov. 7, 2005 (IL) .......................................... 171813

(51) Int. Cl.
*A61K 9/22* (2006.01)
(52) U.S. Cl.
USPC ...................................................... 604/890.1
(58) Field of Classification Search
USPC .................... 604/890.1, 151, 93.01
See application file for complete search history.

(56) References Cited

U.S. PATENT DOCUMENTS

| 3,631,847 | A | 1/1972 | Hobbs, II |
| 3,771,694 | A | 11/1973 | Kaminski |
| 4,197,852 | A | 4/1980 | Schindler et al. |

(Continued)

FOREIGN PATENT DOCUMENTS

| EP | 0 182 502 A2 | 5/1986 |
| EP | 0239244 A1 | 9/1987 |
| EP | 1 177 802 B1 | 2/2002 |
| EP | 1495775 A1 | 1/2005 |

(Continued)

OTHER PUBLICATIONS

International Search Report, Application No. PCT/IL2006/001276 date of mailing Feb. 21, 2007.

(Continued)

*Primary Examiner* — Kevin C Sirmons
*Assistant Examiner* — Deanna K Hall
(74) *Attorney, Agent, or Firm* — Mintz Levin Cohn Ferris Glovsky and Popeo, P.C.

(57) ABSTRACT

Embodiments of the invention are directed to systems, methods and devices for sustained medical infusion with controlled rate injection of a fluid into a body. Such a system may include a first separate reusable unit, a second separate depletable unit a third separate disposable unit having a cannula, and may include a fourth separate remote control unit. Emission of appropriate instructions from the fourth unit, when the first unit, the second unit, and the third unit are coupled together in associative operation and disposed on the skin, power is supplied to an engine for generating motion to a fluid transfer system, and when the cannula is inserted in the body, fluid is transferred from the reservoir to the body, via the tube and the cannula.

21 Claims, 11 Drawing Sheets

(56) References Cited

U.S. PATENT DOCUMENTS

| | | |
|---|---|---|
| 4,498,843 A | 2/1985 | Schneider et al. |
| 4,544,369 A | 10/1985 | Skakoon et al. |
| 4,657,486 A | 4/1987 | Stempfle |
| 4,715,786 A | 12/1987 | Wolff et al. |
| 5,545,143 A | 8/1996 | Fischell |
| 5,558,639 A | 9/1996 | Gangemi et al. |
| 5,957,895 A | 9/1999 | Sage et al. |
| 6,589,229 B1 | 7/2003 | Connelly et al. |
| 6,740,059 B2 | 5/2004 | Flaherty |
| 6,749,587 B2 * | 6/2004 | Flaherty ................. 604/151 |
| 6,960,192 B1 | 11/2005 | Flaherty et al. |
| 7,935,104 B2 * | 5/2011 | Yodfat et al. ............. 604/890.1 |
| 2002/0169439 A1 | 11/2002 | Flaherty |
| 2004/0044306 A1 | 3/2004 | Lynch et al. |

FOREIGN PATENT DOCUMENTS

| | | |
|---|---|---|
| JP | 62201159 A | 9/1987 |
| JP | 2004632670 A | 10/2004 |
| WO | WO-0240083 A2 | 5/2002 |
| WO | WO-02068015 A2 | 9/2002 |
| WO | WO 03/026726 A1 | 4/2003 |

OTHER PUBLICATIONS

International Preliminary Report on Patentability, Application No. PCT/IL2006/001276, date of mailing Jan. 31, 2008.

Communication for corresponding European Application No. 06809836.7, dated Mar. 11, 2009.

* cited by examiner

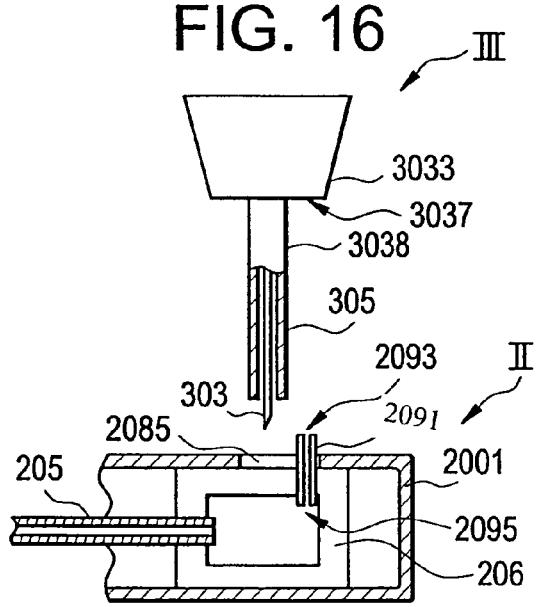
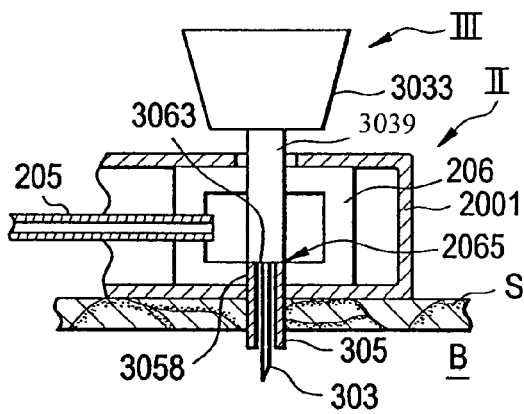
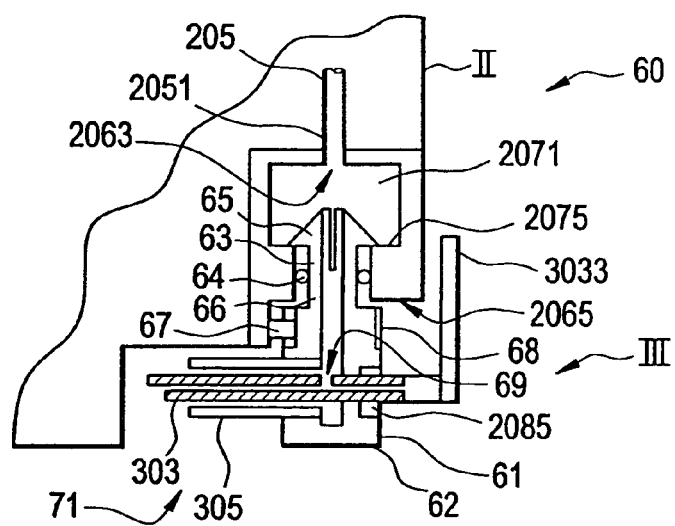

SYSTEMS AND METHODS FOR SUSTAINED MEDICAL INFUSION AND DEVICES RELATED THERETO

CROSS REFERENCE TO RELATED APPLICATIONS

This application is a continuation of U.S. patent application Ser. No. 11/397,115, filed on Apr. 3, 2006 now U.S. Pat. No. 7,935,104, which claims priority to and benefit of Israeli patent application no. 171813, filed on Nov. 7, 2005, the entire disclosures of which are herein incorporated by reference.

BACKGROUND OF THE INVENTION

1. Field of the Invention

Embodiments of the present invention relate generally to a method, a system and various devices for sustained medical infusion of fluids, and more particularly, to a system having a portable infusion device (preferably miniature) adherable directly to a patient's skin, and to associated methods and devices for accurate dispensing of fluids from the device into the body of the patient. Some embodiments of the present invention relate to the connection of two or more separate portions (e.g., planar connection), such as a disposable portion and a reusable portion, preferably forming a flexible, pliable and thin skin-compliant device (e.g., patch).

2. Background of the Invention

Medical treatment of several illnesses requires continuous drug infusion into various body tissues, through subcutaneous and intra-venous injections (for example). Diabetes mellitus patients require the administration of varying amounts of insulin throughout the day to control blood glucose levels. In recent years, ambulatory portable insulin infusion pumps have emerged as a superior alternative to multiple daily injections of insulin. These pumps, which deliver insulin at a continuous basal rate as well as in bolus volumes, were developed to liberate patients from repeated self-administered injections, and allow them to maintain a near-normal daily routine. Both basal and bolus volumes must be delivered in precise doses, according to an individual prescription, since an overdose of insulin could be fatal. Therefore, insulin injection pumps must be highly reliable to prevent delivery of any unintentional excess insulin.

Several ambulatory insulin infusion devices are currently available on the market. Generally, these devices have two parts: a reusable portion, containing a dispenser, a controller and electronics, and a disposable portion containing a reservoir, a needle assembly, with cannula and trocar, and a fluid delivery tube. The insertion of a variety of needles of different length and insertion angles, as required by the location of the injection on the body, demands a great deal of skill and practice. Usually, the patient fills the reservoir, attaches the needle and the delivery tube to the exit port of the reservoir, and then inserts the reservoir into the pump housing. After purging air out of the reservoir, the tube and the needle, the patient inserts the needle assembly, trocar and cannula, at a selected location on the body, and withdraws the trocar. To avoid irritation and infection, the subcutaneous cannula must be replaced and discarded after two to three days, together with the empty reservoir.

Examples of first generation disposable syringe-type reservoir and tubes were described in 1972, by Hobbs, in U.S. Pat. No. 3,631,847, and in 1973, by Kaminski, in U.S. Pat. No. 3,771,694, and later by Stempfle, in U.S. Pat. No. 4,657,486, and by Skakoon, U.S. Pat. No. 4,544,369. The driving mechanism of these devices is a screw thread driven plunger controlling the programmed movement of a syringe piston. Other dispensing mechanisms have been described including peristaltic positive displacements pumps, for example in 1980, by Wilfried Schal et al, in U.S. Pat. No. 4,197,852, and later by Schneider, in U.S. Pat. No. 4,498,843, and by Wolff, in U.S. Pat. No. 4,715,786.

These devices represent a significant improvement over multiple daily injections, but all suffer from several drawbacks. The main drawback is the large size and the weight of the device, caused by the spatial configuration and the relatively large driving mechanism of the syringe and the piston. The relatively bulky device had to be carried in a patient's pocket or attached to a belt. Consequently, the fluid delivery tube is long, usually longer than 40 cm, to permit needle insertion in remote sites of the body. These uncomfortable bulky devices with a long tube are rejected by the majority of diabetic insulin users, since these devices disturb regular activities, such as sleeping and swimming for example. Furthermore, the effect of the image projected on a teenagers' body is unacceptable.

In addition, the delivery tube excludes some optional remote insertion sites, like the buttocks and the extremities. To avoid the tubing limitations, a second generation of such devices has been devised. These devices included a housing having a bottom surface adapted for contact with the patient's skin, a reservoir disposed within the housing, and an injection needle adapted for communication with the reservoir.

This paradigm was described by Schneider, in U.S. Pat. No. 4,498,843, Sage in U.S. Pat. No. 5,957,895, Connelly, in U.S. Pat. No. 6,589,229, and by Flaherty in U.S. Pat. Nos. 6,740,059 and 6,749,587, none of them being currently available on the market. The above-mentioned second-generation devices have several limitations. They are bulky, because the reusable dispensing portion including the driving mechanism, is assembled on top of the disposable needle/reservoir portion. Such a "sandwich shaped" design, and their stacking in at least two layers, leads to a relatively thick device having thickness of between 15 to 20 mm. Moreover, upon the needle emerging from the bottom of the device during insertion (either manually or automatically), the needle is usually inserted perpendicular to the skin (e.g., a predetermined angle) that for most patients is inconvenient and requires some skill to accomplish. The device was abandoned by patients wanting to see the puncture site and preferring needle insertion angles of less than 30°.

Second-generation devices with a positive displacement peristaltic dispenser, e.g. Flaherty in U.S. Pat. No. 6,749,587, are provided with the drive mechanism and engine contained within the reusable portion, which is positioned on top of the pumping wheel, contained within the disposable portion. This configuration exhibits major limitations that are associated with inefficient energy utilization, and constant, long term pressure of the pump's wheel(s) applied on a transfer tube during the entire shelf life of the dispenser. Due to long term pressure the operation of the dispenser might be associated with inaccuracies because of the creeping of plastic material, from which the transfer tube is made. Another disadvantage of the above-mentioned configuration is associated with the fact that it allows air purging only after assembling of all the parts of the dispenser and requires operating the engine.

Other drawbacks of second-generation devices include leaking connections between reusable and disposable portions, as well as unavailable water resistance. Finally, a major limitation for the widespread acceptance of first and second generation pumps is their extremely high purchase price, running from $4000 to $6000, and maintenance costs amounting to some $250 per year.

Thus, there is a need for a miniature portable programmable fluid dispenser having an insertion needle which does not require direct connection with a connecting tube, and that allows direct adhesion to the patient's skin at any desired location on the body, and that could be remotely controlled. Preferably, the disposable portion of the device should contain a reservoir allowing manual filling and purging of air. After connection of the reusable and the disposable portions, the thickness of the unified device should be small (e.g., less than five (5) mm). Furthermore, the reusable portion should contain a high precision peristaltic pump for very accurate dispensing doses of fluid.

SUMMARY OF THE INVENTION

Embodiments of the present invention address the above-noted concerns and present methods, systems and devices for sustained medical infusion of beneficial and therapeutic liquids into a body of a patient, preferably in a programmed mode of highly accurate doses delivered by a skin-adherable and preferably compliant flexible device (e.g., patch).

It is object of some of the embodiments of the present invention to provide a method for sustained medical infusion with controlled rate injection of a liquid into a body of a patient. Such a method may comprise one or more of the following steps:

providing a first separate, reusable unit, preferably comprising:
  a controller for managing operations,
  a transceiver for communication,
  an engine for generating motion for a fluid transfer system, and
  a first portion (preferably main portion) of a fluid transfer system, the fluid transfer system becoming operative for transfer of liquid when the first portion is coupled to a secondary portion;

providing a second separate depletable unit preferably comprising:
  a secondary portion of the fluid transfer system, for coupling to the first portion,
  a reservoir of liquid to be infused,
  optionally providing a well,
  a tube to enable communicating fluid from the reservoir to the body of the patient, and
  at least one battery for delivery of power to the first unit when the first unit is operatively coupled to the second unit;

providing a third unit preferably comprising:
  a cannula, and
  a trocar fitted to the cannula for inserting the cannula into skin and body; and providing a fourth separate remote control unit preferably comprising:
  a transceiver for communication with the first unit,
  at least one memory for storing at least one of one or more computer program, data, and instructions,
  a command and control module coupled to the memory and to the transceiver, and operative for receiving, executing, and emitting data and instructions, and
  an I/O user interface for communication of data to a user and for sending instructions from the user to the controller and transceiver.

Upon emission of appropriate instructions from the fourth unit, when (preferably) all three of the first unit, the second unit, and the third unit are coupled together in associative operation and disposed on the skin of the patient, power is supplied to the engine for generating motion to the fluid transfer system, and upon the cannula being inserted into the body of the patient, liquid is transferred from the reservoir to the body, control of the controller and transceiver.

It is yet another object of some of the embodiments of the present invention to provide a method for sustained medical infusion where a first portion of a fluid transfer system is disposed in a first unit, a second portion of the fluid transfer system is disposed in a second unit, and coupling of the first unit in operative association with the second unit renders the fluid transfer system operational to eject fluid.

It is yet another object of the present invention to provide a method for sustained medical infusion where a first unit of a fluid dispenser and a second unit of the fluid dispenser, are releasably connectable, and each of the first and the second unit may be configured as flexible, skin-compliant envelope, and at least the second unit is releasable adherable to the skin. Each envelope may also be transparent.

It is yet another object of some of the embodiments of the present invention to provide a method for sustained medical infusion where each one of a first unit, a second unit, and a third unit may come in different types depending upon the required treatment, though still connectable together to form a dispensing device (i.e., each type of each unit is interchangeable for use with a number of types of other units).

It is yet another object of some of the embodiments of the present invention to provide a method for sustained medical infusion where a first portion of a fluid transfer system exerts pressure on a tube to allow flow of fluid therethrough only when the first portion is operatively coupled to the secondary portion.

It is yet another object of some of the embodiments of the present invention to provide a method for sustained medical infusion where the reservoir may be filled manually, and air may be purged manually out of at least one of a reservoir, a tube, and a well.

It is yet another object of some of the embodiments of the present invention to provide a method for sustained medical infusion where a cannula is insertable at any desired angle ranging from zero degrees to 90 degrees.

It is yet another object of the present invention to provide a method for sustained medical infusion where at least one sensor is disposed on either one of both, or in both, a first unit of a fluid dispenser and a second unit of the fluid dispenser to provide feedback signals to the controller and transceiver.

It is yet another object of some of the embodiments of the present invention to provide a system for sustained medical infusion with controlled rate injection of a liquid into the body of a patient. Such a system may include one or more of the following, and preferably includes a majority or all of the following:

a first separate reusable unit, preferably comprising:
  a controller for managing operations,
  a transceiver for communication,
  an engine for generating motion for a fluid transfer system, and
  a first (e.g., main) portion of a fluid transfer system, the fluid transfer system becoming operative for transfer of liquid when coupled to a secondary portion;

a second separate depletable unit, preferably comprising:
  a secondary portion of the fluid transfer system, for coupling to the first portion,
  a reservoir of liquid to be infused,
  optionally a well,
  a tube to enable communicating fluid from the reservoir to the body of the patient, and at least one battery for delivery of power to the first unit when the first unit is operatively coupled to the second unit;
a third unit, preferably comprising:
    a cannula, and
    a trocar fitted to the cannula for inserting the cannula into skin and body; and
a fourth separate remote control unit, preferably comprising:
    a transceiver for communication with the controller and transceiver,
    at least one memory for storing at least one of one or more computer programs, data, and instructions,
    a command and control module coupled to the memory and to the transceiver and operative for receiving, executing, and emitting data and instructions, and
    an I/O user interface for communication of data to a user and for sending instructions from the user to the controller and transceiver.

Upon emission of appropriate instructions from the fourth unit, when all three of the first unit, the second unit, and the third unit are preferably coupled together in associative operation and disposed on the skin of the patient, power is supplied to the engine for generating motion for the fluid transfer system, and when the cannula is inserted into the body of the patient, liquid is transferred from the reservoir to the body, via the tube and the cannula, under control of the controller and transceiver.

It is yet another object of some of the embodiments of the present invention to provide a system for sustained medical infusion taking advantage of the method steps described hereinabove.

It is yet another object of the present invention to provide one or more devices for sustained medical infusion with controlled rate injection of a liquid into the body of a patient, the devices preferably comprising:
a first separate reusable device, preferably comprising:
    a controller for managing operations,
    a transceiver for communication,
    an engine for generating motion for a fluid transfer system, and
    a first (e.g., main) portion of the fluid transfer system, the fluid transfer system becoming operative for transfer of liquid when coupled to a secondary portion;
a second separate depletable device, preferably comprising:
    a secondary portion of the fluid transfer system, for coupling to the main portion,
    a reservoir of liquid to be infused,
    optionally a well,
    a tube to enable communicating fluid from the reservoir to the body of the patient, and
    at least one battery for delivery of power to the first device when the first device is operatively coupled to the second device;
a third device, preferably comprising:
    a cannula for insertion into the body of a patient, and
    a trocar fitted to the cannula for inserting the cannula into skin and body; and
a fourth separate remote control device, preferably comprising:
    a transceiver for communication with the controller and transceiver,
    at least one memory for storing at least one of one or more computer programs, data, and instructions,
    a command and control module coupled to the memory and to the transceiver and operative for receiving, executing, and emitting data and instructions, and
    an I/O user interface for communication of data to a user and for sending instructions from the user to the controller and transceiver.

Upon emission of appropriate instructions from the fourth device, when all three of the first device, the second device, and the third device are preferably coupled together in associative operation and disposed on the skin, power is supplied to the engine for generating motion for the fluid transfer system, and when the cannula is inserted into the body of the patient, liquid is transferred from the reservoir to the body, via the tube and the cannula, under control of the controller and transceiver.

These and other embodiments, advantages and objects of the invention will become even more clear in view of the following detailed description and attached drawings, a brief description of which is set out below.

BRIEF DESCRIPTIONS OF THE DRAWINGS

FIG. 16 illustrates a depletable unit II having a vent tube, and an injection unit III according to some embodiments of the present invention.

FIG. 17 illustrates a depletable unit II and an injection unit III according to some embodiments of the present invention.

FIG. 18 illustrates a partial cross sectional plan view of a depletable unit II according to some embodiments of the present invention.

DETAILED DESCRIPTION OF THE EMBODIMENTS

Figure 1:
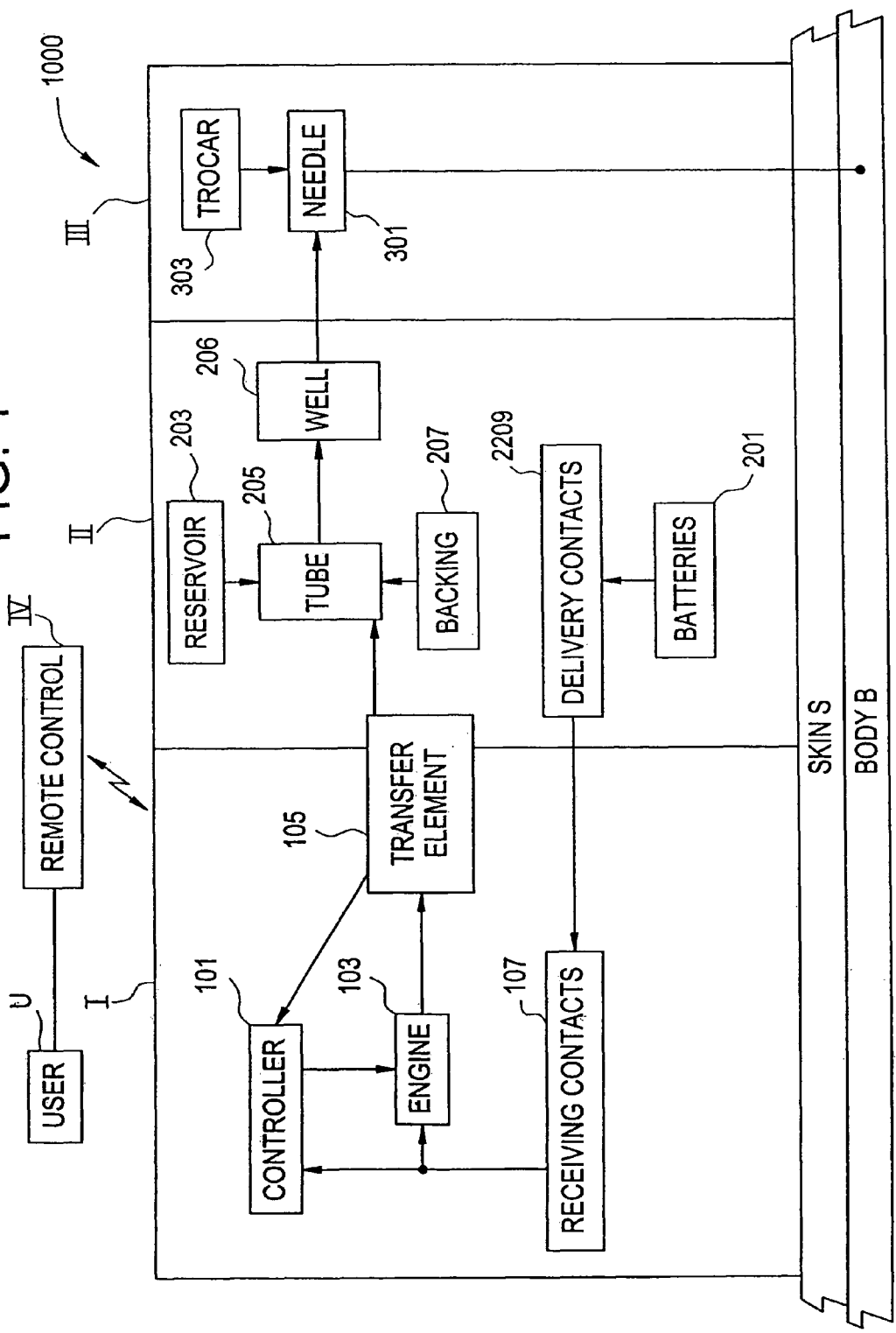
FIG. 1 illustrates a block diagram of a fluid delivery system according to some embodiments of the present invention.

FIG. 1 is a block diagram of an exemplary system 1000 for implementing a sustained controlled injection (preferably at a predetermined rate) of a liquid into the skin or subcutaneously into the body of a patient. The term "body B" is regarded as meaning: subcutaneously into the body B, and may also refer to intravenous injection.

The system 1000 includes a reusable unit I, a depletable unit II, an injection unit III, and a remote control unit IV (unit IV), which preferably are separate units. Unit I and unit IV are each reusable, while the depletable unit II and the injection unit III are both preferably disposable and together may form a disposable portion or unit that is discarded after one single use. Units I, II and III together form a fluid dispensing device.

The following description of the operation of system 1000 is merely for example only, and one of skill in the art will appreciate that other methods of operation are within the scope of this and related embodiments of the invention. Accordingly, a user U selects a reusable unit I and a depletable unit II, and programs the system 1000, preferably by use of the remote control unit IV. The depletable unit II may then be filled with a desired liquid and upon purging of air be coupled to the reusable unit I. An injection unit III is selected and preferably introduced into the depletable unit II. Optionally, the injection unit III may be integral with the depletable unit II. After purging of air, units I, II and III are applied onto and preferably adhered to the skin S, while a needle pierces through the skin S, and into the body B. Units I and II may be flexible envelopes, possibly transparent, with at least unit II being releasably adherable to the skin S.

The remote control unit IV may then be operated to program the fluid dispensing device to command flow of the liquid from the depletable unit II and into and preferably through the skin S (i.e., subcutaneously) into the body B. The user U is either an operator applying the system 1000 on a body, or a patient helping himself.

As shown in FIG. 1, unit I may include one or more (and preferably all), generally, of the following components: a control, command and transceiver module 101 (or controller and transceiver 101), for control and communication in the management of fluid injection, and for bi-directional communication with the remote control unit IV. Also included in unit I may be an engine 103 for imparting motion to a fluid transfer element 105 of a fluid transfer system, or transfer element 105 for short. The fluid transfer system preferably comprises components belonging to both unit I and unit II. Specifically, the fluid transfer system may comprise the engine 103, the fluid transfer element 105, a flexible tube 205 and a backing plate 207, the latter two elements being preferably included in unit II. For the engine 103 and the transfer element 105 to become operative, unit I preferably is first coupled to the depletable unit II, to obtain power therefrom, and because the transfer element 105 operates in conjunction with the tube 205 and backing plate 207 contained in unit II.

The transfer element may have a first, main portion disposed in the first unit I, and a secondary portion disposed in the second unit II. When the first unit I and the second unit II are coupled in operative association, transfer of fluid out of the second unit II may occur, on condition that power is supplied to the engine 103.

The depletable unit II preferably includes, in general, one or more batteries 201 for powering the reusable unit I, a reservoir 203, which either comes pre-filled with the liquid for dispensing or is filled with the liquid prior to use, and a tube 205 coupled to the reservoir for delivery of the liquid to a well 206. The liquid, which is not shown in the figures is injectable only after the injection unit III is coupled to provide fluid communication with the depletable unit II and the injection unit III is inserted into skin S or body B.

The injection unit III includes mainly a needle 301, which is preferably assembled to other elements, preferably a trocar 303. For the injection of liquid, the injection unit III is inserted into the depletable unit II, at well 206. Well 206 is coupled in fluid communication with the tube 205. The needle 301 is inserted through the well 206 and into the body B through the skin S. Then, the trocar 303 may be retrieved and fluid is injected, as dosed and dispensed at a predetermined rate by the fluid transfer system. The liquid may be a beneficial fluid or a therapeutic agent.

There may be various types of each one of the three units I, II, and III, where each one type of the same unit (i.e. I, II, or III), being interchangeable and replaceable with the other type. The different types of units I, II, and III may all be configured to be releasable coupled for operation.

For example, diverse types of reusable units I may include a controller and transceiver module 101 with a chosen level of sophistication and optionally, an I/O pad and/or connection, a safety sensor, and may include further options. Likewise, different types of depletable units II may have a reservoir 203 of different size, batteries of diverse capacity, and contain an alternative liquid. Similarly, the injection unit III may have a needle that is shorter, longer, be suitable for insertion at an angle or perpendicularly to the skin, or be of a different kind, according to needs.

Regardless of their type, the various components of the reusable units I and of the depletable units II are preferably all disposed as a single layer, arranged and supported on the same plane, and preferably so are their corresponding connections and couplings. When assembled and adhered to the skin S, side-by-side along their thickness dimension (i.e., in end-to-end disposition), the two units I and II preferably cover an area not larger than about half the size of a plastic credit card (or smaller), or typically a region measuring about 65 mm by about 25 mm. Unit III preferably does not add to the covered area.

Both the reusable unit I and the depletable unit II are preferably hermetically sealed and each may form a flexible envelope that remains sealed even while in use. In one particular embodiment, one face or surface of the envelope of unit I and of unit II may be configured for application in mutual assembly to the skin S, as a skin conforming patch, at most some 4 mm high (for example). Actually, the reusable unit I may be releasably latched to unit II, and at least unit II (but also unit I if desired), may releasably adhere to the skin S.

The needle 301 may differ in length according to type. For example, needle 301 may be sized to penetrate subcutaneously for only 3 mm, or as deep as 30 mm. After removal of the trocar 303, the height of the skin-attached units preferably does not increase.

The mechanism for fluid transfer exemplifies the associative operation of the units I, II, and III. In principle, according to one embodiment of the invention, the fluid transfer system is a peristaltic positive displacement pump—where the fluid transfer tube 205 is squeezed to transfer fluid from the reservoir for injection to the body of the patient. The first (main) portion of the peristaltic positive displacement pump, as well as the engine 103 to drive that pump, may be included in unit I. However, the tube 205, the backing 207, the liquid in the reservoir 203, and batteries 201 for driving unit I, may be included in the depletable unit II. In some embodiments, actual injection of the liquid is possible only when at least the units I and II are coupled together for operation.

Figure 2:
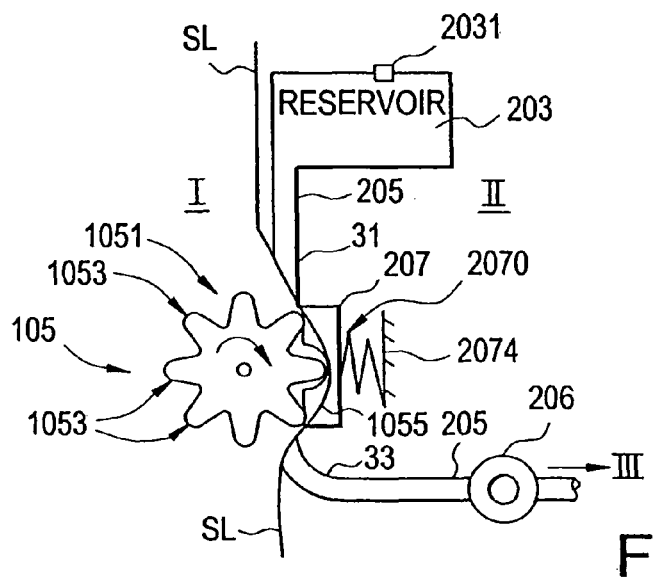
FIG. 2 is a schematic diagram of an edge portion of a first unit coupled to a second unit of a fluid dispensing device according to some embodiments of the present invention.

FIG. 2 is a schematic illustration showing an edge portion of unit I when attached to unit II, illustrating an exemplary fluid transfer system according to some embodiments of the invention. A single toothed wheel, or cogwheel 1051, or gear 1051, with teeth 1053, is appropriately disposed to compress the exterior wall of the flexible tube 205, which is seen be coupled to and exiting out of the reservoir 203. The tube 205 is compressed between the teeth 1053 of the gear 1051 and backing 207 disposed adjacent and tangentially to the gear 1051. Optionally, the backing may comprise a flat or curved back plate 207. Preferably, the backing 207 is loaded by a spring 2070 biased against a static base 2074.

While the engine 103 rotates the gear 1051, clockwise as seen in FIG. 2, a quantum of fluid 1055, trapped between two adjacent teeth 1053 of the gear 1051, is transferred along the tube. Transfer of liquid occurs from an upstream suction side 31, adjacent the reservoir 203, to a discharge side 33 downstream of the transfer element 105, leading the liquid to well 206, and eventually to the needle in unit III. The flexile tube 205 extends between the reservoir 203 and the well 206.

When unit I is not coupled to unit II (during non-use), no pressure or forces are applied to the tube 205, thereby rendering the shelf-life of the tube longer.

Various types of engines 103 may be used, some examples being described hereinbelow. Regardless of type, the engine 103 may be operated continuously, or at appropriately selected time intervals, according to the rate of fluid to be dispensed.

When appropriately selected, the fluid transfer system including the gear 1051, backing 207, and teeth 1053, substantially guarantees and preferably permanently prevents a direct flow, in either or both directions, to the suction side 31 or the discharge side 33, thereby enhancing safety of use. Accordingly, such fluid transfer systems, according to some embodiments of the present invention, allow control of the direction of flow of the fluid without requiring valves; as long as at least one tooth 1053 completely compresses the tube 205 and blocks the passage of liquid, no valves are required. Use of the foregoing positive displacement pump is not associated with backpressure, and thus, backpressure drop will not occur.

In some embodiments of the present invention, the dispenser delivers the infused fluid in discrete, equal-sized volumes of between about 0.2-1 of $10^{-4}$ cc per roller or tooth 1053. Flow rate may therefore be provided in minute quanta and can be precisely controlled simply by regulating the speed of rotation of the wheel 1051. In other words, flow rate can be measured simply by counting rollers, or teeth, as they rotate past the tube 205. In the various driving wheel configurations, at least one roller, or tooth 1053, preferably always depresses tube 205, which substantially eliminates (and preferably eliminates) a hydraulic "short circuit" (i.e., direct communication between the reservoir and the well 206).

A desired flow rate of liquid may be obtained according to the number of teeth 1053 rotated per unit of time. Assuming that the gear 1051 rotates to depress the tube 205 at a rate of n teeth per minute, and that a basic volume $v_t$ mm$^3$, or quantum of fluid 1055, is trapped between two adjacent teeth 1053 of the gear 1051, then the pumped rate of flow of liquid may be calculated as follows:

$$\text{Flow rate} = n \cdot v_t \, [\text{mm}^3/\text{minute}] \quad (1)$$

Here "n" ranges from 0 to a maximum, and $v_t$ is defined according to the selected configuration of the cogwheel 1051. High accuracy of the quantity of transferred liquid may thus be achieved by programming the controller and transceiver 101, to appropriately control the parameter n for a given $v_t$.

The reservoir 203 is preferably configured either as a flexible container, or as a resilient collapsible and expandable bladder (or other collapsible fluid retention device). The reservoir 203 may include a self-sealing filling port 2031, permitting a user U to fill the reservoir using a syringe (not shown in the drawings). To that end, the user U selects a desired liquid, and fills the syringe. Then, the needle of the syringe is used to pierce the self-sealing filling port 2031 of the reservoir 203, and the selected liquid is injected into the container 203, or bladder 203, which expands during filling up to a maximal volume.

When the reservoir 203 is filled to capacity, liquid will continue to flow, to also fill the tube 205, and finally, exit out of the well 206. By virtue of this provision, the user U may manually purge air out of the unit II prior to using the device. After filling the reservoir 203, the syringe is evacuated from the filling port 2031, which self-seals the reservoir.

The reservoir 203 is preferably manufactured integrally with the tube 205, or hermetically attached thereto by virtue of a conventional connector (not shown in the figures). Optionally, the reservoir 203 may be provided readily prefilled from factory.

The expansion of the bladder type reservoir 203 may be limited, say by a cage or by an enclosure not shown in the figures, or left free to expand until arrested by a component of unit II or a housing thereof. In some embodiments, when left free, the bladder type reservoir 203 may expand in all directions and penetrate into available interstices, even filling gaps remaining open between components, taking maximum advantage of unused space.

In FIG. 2, the separation line SL indicates the abutting edges of unit I and unit II, clearly illustrating that fluid transfer will not occur when units I and II are separated, because the wheel 1051 will be distanced away from the tube 205, and the engine 103 will be deprived of power received from the batteries 201.

Each unit may comprise a specific type for a specific application/treatment. To that end, each type may be distinguished from another by, for example, fluid contents, a reservoir 203 of chosen size, and/or batteries of given power.

Figure 3:
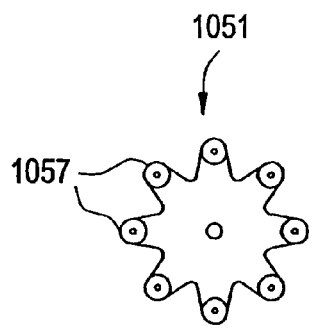
FIG. 3 illustrates a first portion of a fluid transfer system according to some embodiments of the present invention.

FIG. 3 illustrates another embodiment of the wheel 1051, with freewheeling rollers 1057 supported at the extremities of all the teeth 1053, to provide for low rolling friction.

Figure 4:
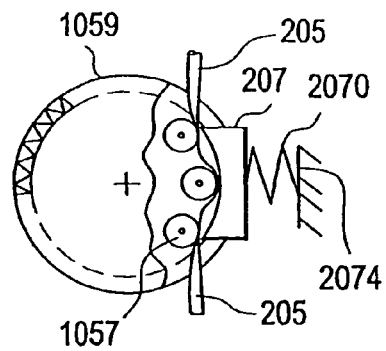
FIG. 4 illustrates a partial cross-section view of portions of a fluid transfer system according to some embodiments of the present invention.

FIG. 4 depicts a partial cross-section of a further embodiment, where the rollers 1057 are supported freely and rotatably between two plates 1059. The outer circumference of the plates 1059 may exceed that of the rollers 1057, so that the diameter of the tube 205 is partially or completely disposed between the two plates 1059. The plates 1059 may be geared for engagement with other geared driving means. If desired, only one plate 1059 with rollers 1057 is sufficient. Other embodiments of support plate are possible.

Figure 5:
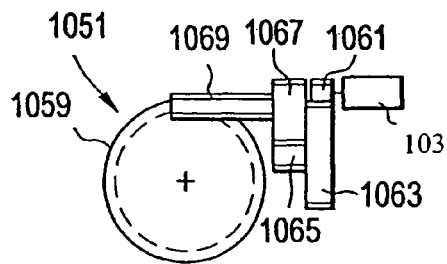
FIG. 5 illustrates a transmission system for transferring rotational motion in a fluid transfer system according to some embodiments of the present invention.

FIG. 5 illustrates an example of a transmission of rotational motion from the motor 103, via reduction gears, to a gear 1051 or to a geared plate 1059. The engine 103, here motor 103, drives a first spur gear 1061 that engages a second spur gear 1063 of diameter larger than that of gear 1061. A third spur gear 1065, concentrically fixed to and of diameter smaller than that of the second spur gear 1063, engages a fourth spur gear 1067, of diameter larger than that of the third spur gear 1065, to which a worm gear 1069 is affixed concentrically. At the end of the reduction train, the worm gear 1069 rotates the gear 1051.

Figure 6:
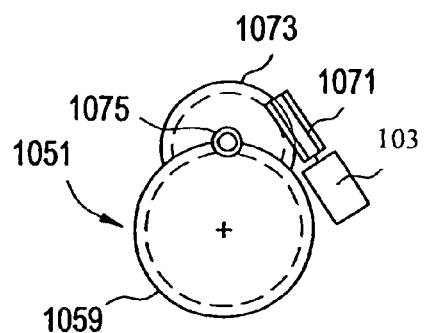
FIG. 6 illustrates a transmission system for transferring rotational motion in a fluid transfer system according to some embodiments of the present invention.

FIG. 6 is another example of a gear train reduction mechanism. The motor 103 drives a worm gear 1071, which engages a spur gear 1073 having a concentrically mounted smaller diameter spur gear 1075 affixed thereto. That last spur gear 1075 rotates the gear 1051 or the plate 1059. Other transmission configurations are possible, by friction, gears, and flexible shafts, for example.

Figure 7:
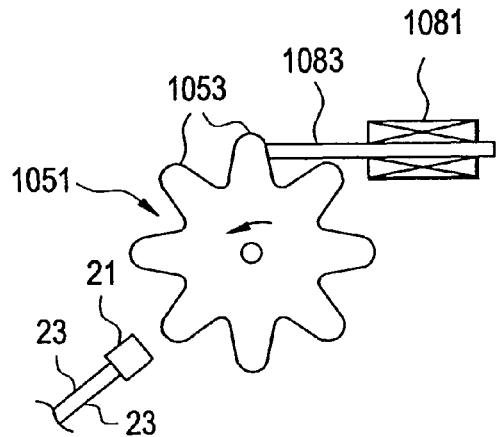
FIG. 7 illustrates a linear actuator for use with a fluid transfer system according to some embodiments of the present invention.

FIG. 7 presents a linear actuator 1081, such as a solenoid, with a reciprocating plunger 1083 striking a tooth 1053 to drive the wheel 1051 counterclockwise.

Figure 8:
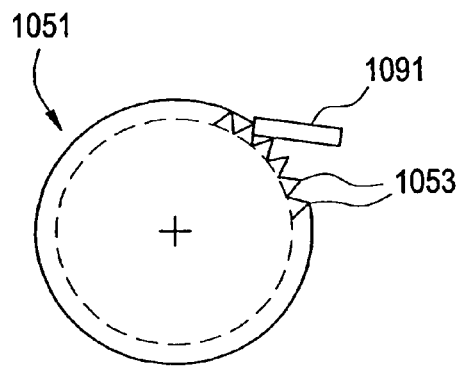
FIG. 8 illustrates a piezo-electric actuator for use with a fluid transfer system according to some embodiments of the present invention.

FIG. 8 shows a piezoelectric actuator 1091 tangentially engaging a tooth 1053 on the periphery of a wheel 1051 or plate 1059 for providing counterclockwise rotation. A pulse of power causes the piezoelectric actuator 1091 to deliver one tangential strike to a tooth 1053, and to rotate the wheel 1051.

Other transmission and reduction mechanisms may also be possible, which may utilize planetary, rolling, and friction gears, rack and teeth mechanisms, and belts, whether alone or in combination.

To report proper rotation of the wheel 1051 pertaining to the transfer element 105 to the controller and transceiver 101, a simple reusable sensor may be optionally mounted on unit I.

Figure 9:
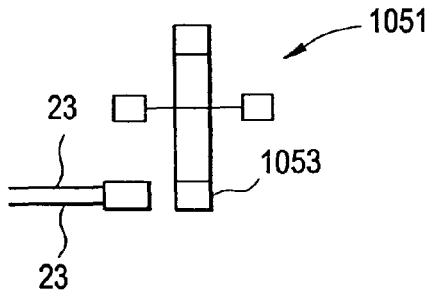
FIG. 9 illustrates a reusable sensor for a fluid transfer system according to some embodiments of the present invention.

FIG. 7 shows schematically a reusable sensor 21 which may be used in embodiments of the present invention and which is disposed opposite a tooth 1053, in the plane of the wheel 1051. One or more leads 23 connect between the sensor 21 and the controller and transceiver 101. The reusable sensor 21 is selected as an appropriate component of a type known in the art, such as capacitive, inductive, magnetic, mechanic, or optic sensor, or a combination thereof. In one embodiment, the reusable sensor 21 is disposed opposite a tooth 1053, as shown in FIG. 9. To this end, the controller and transceiver 101 may compare the commanded rotation rate of the wheel 1051 with the output of the reusable sensor 21, and emit correction signals to the transfer element 105 (if necessary).

In FIG. 1, an arrow coupling from the transfer element 105 to the controller and transceiver 101 indicates feedback, for use in some embodiments, allowing the controller to respond accordingly when necessary. The reliability of the system 1000 is thereby enhanced.

In some embodiments, irrespective of the kind of engine 103 or fluid transfer element 105 used in the fluid transfer system, when unit II is coupled to unit I, the batteries 201 in unit II are electrically connected to delivery contacts 2209, which may be appropriately disposed to couple with the receiving contacts 107 disposed in unit I. In turn, the receiving contacts 107 may be connected to the controller and transceiver 101, and to the engine 103, which actuates the fluid transfer element 105. After use and depletion, unit II is discarded and replaced, while unit I may be reusable.

Figure 10:
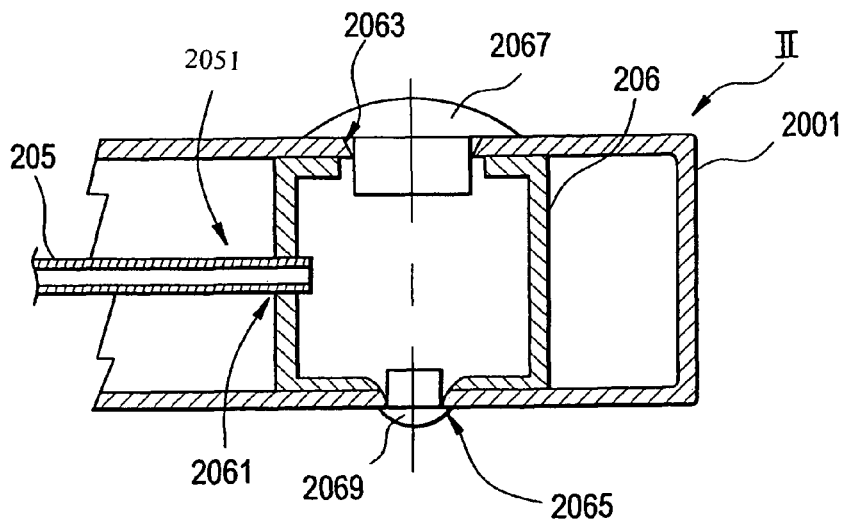
FIG. 10 illustrates a partial cross sectional view of a depletable unit II according to some embodiments of the present invention.

FIG. 10 is a partial cross-section of a portion of the depletable unit II according to some embodiments, showing the envelope 2001, the downstream extremity 2051 of the flexible tube 205, which is coupled in fluid communication to the well 206. When the well 206 is filled with the liquid it may be supplied for injection via the injection unit III. The well 206 functions as a receptacle for the liquid and it is provided with a tube inlet 2061 to which the downstream extremity 2051 of the tube 205 is attached, with an entry aperture 2063, and with an exit aperture 2065.

In FIG. 10, the entry aperture 2063 and the exit aperture 2065 are preferably releasably and hermetically sealed by, respectively, an entry plug 2067 and an exit plug 2069. A peel-off label, or other sealing means, may be provided instead of the entry plug 2067 and the exit plug 2069.

The well 206 may extend from the entry aperture 2063 to the exit aperture 2065, being substantially directed across the whole height of unit II, and may also be perpendicular to the tube 205. The exit aperture 2065 may be flush with the proximal surface of unit II to be adhered to the skin S, and the entry port 2063 may open on the opposite surface of unit II, which is the distal surface, pointing away from the skin. This disposition of the well 206 may be considered as a vertical disposition.

With liquid in the reservoir 203, and before using the system 1000, the depletable unit II is coupled to the reusable unit I. Then, as shown in FIG. 10, the exit plug 2069 may be removed, whereby the exit opening 2065 is exposed and permits passage of liquid. Next, command is provided, say, by use of the remote control unit IV, to enable the dispenser device pump to urge liquid out of the reservoir 203 and into the well 206 via the flexile tube 205 extending between the reservoir and the well. Thereby, liquid is released through the exit opening 2065, so that when unit II is held (appropriately), with the exit aperture 2065 turned upwards (for example), air will be purged out of the unit II. Alternatively, air may be purged manually, prior to coupling, as described hereinabove.

In turn, the entry plug 2067 may be removed so that both the entry aperture 2063 and the exit aperture 2065 may be open to permit free introduction of the injection unit III into the well 206.

Figure 11:
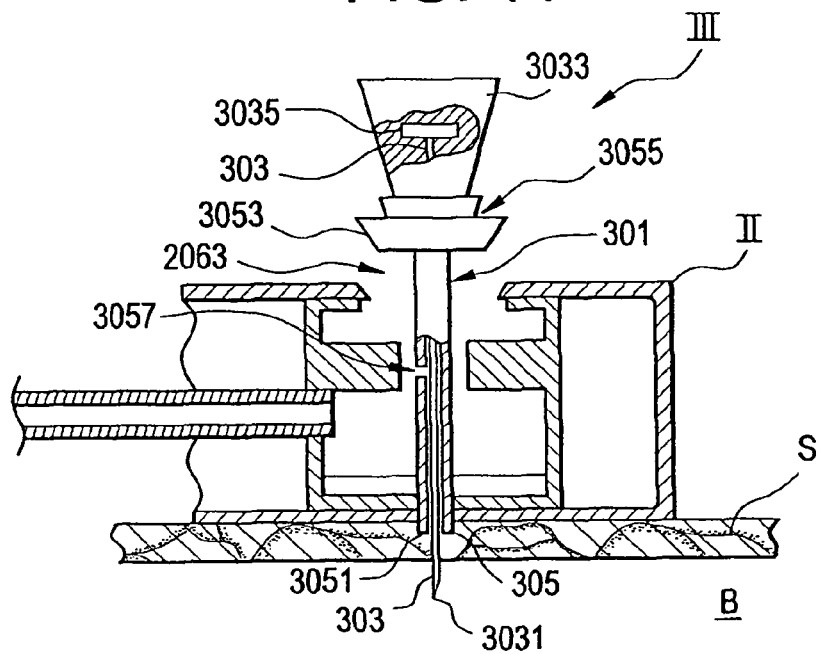
FIG. 11 illustrates a partial cross-sectional view of a depletable unit II, having an injection unit III partially engaged therein according to some embodiments of the present invention.

FIG. 11 shows an example of an injection unit III partially engaged into the depletable unit II. As shown, at the bottom of unit III, the sharp tip 3031 terminates the penetrating extremity of the trocar 303, shrouded by a cannula 305. It is seen that the cannula, has already pierced through the skin S.

For piercing the injection unit III is preferably translated toward and into the unit II, until it is fully engaged and seated therein, and then the trocar 303 is retrieved out and away from the injection unit III, and discarded.

At the top of unit III, a handle 3033 may be fixedly attached to the trocar 303. The handle 3033 itself, as a separate part, is not essential in embodiments of the present invention since the grip extremity 3035 of the trocar 303 may be formed as a handle, for example, as a hook or as a ring. In configurations described hereinbelow, the trocar 303 may have a solid cross-section as a dagger, or be hollow for air purging purposes (for example).

Still in FIG. 11, the cannula 305 is open at the skin-contacting extremity 3051 and is preferably firmly attached to a plug 3053 at the opposite extremity. The plug 3053 may be configured with a rim 3055 to permit only a single one-way insertion via the entry opening 2063 of unit II. At least one radial bore 3057 may be provided into the cannula 305 to permit fluid communication from the interior of the well 206 into the lumen of the cannula.

Figure 12:
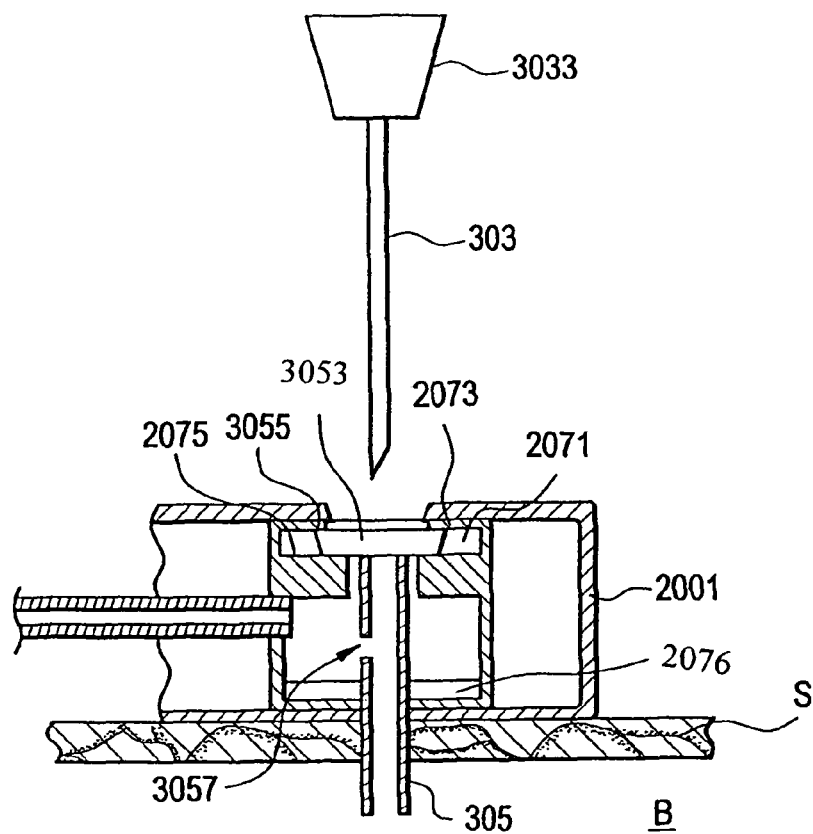
FIG. 12 illustrates another partial cross-sectional view of the depletable unit II and injection unit III shown in FIG. 11.

FIG. 12 depicts the cannula 305 when inserted into the body B and fully seated in unit II, with the trocar being already retrieved. The cannula 305 may be anchored by the plug 3053 in the interior of a trap 2071 formed in unit II. The plug 3053 may be captive between the extension 2073, at the rim 3055, and the step 2075. The plug 3053 seals liquid flowing into the well 206 via the tube 205, to keep it from spilling out of the entry opening 2063.

Likewise, according to some embodiments, the spilling of fluid out of the exit opening 2065 is prevented by the envelope 2001 acting as a seal, or by a dedicated exit seal 2076, or by both. In the same manner, although not shown in the figures, it is possible to use the viscoelastic envelope 2001 to seal the entry opening 2063.

Accordingly, liquid contained inside the well 206 is prevented from escaping via the entry opening 2063 and/or the exit opening 2065, but may flow into the cannula 305 via the radial bore 3057 and out of the cannula via discharge opening 3059. Accordingly, liquid transferred out of the reservoir 203 is provided for injection into the skin S or the body B of the patient.

Figure 13:
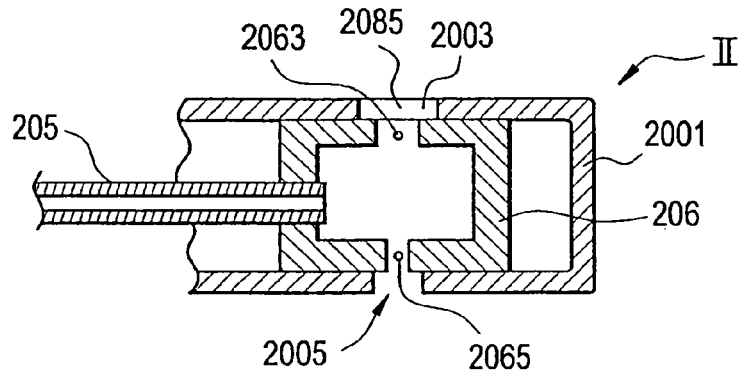
FIG. 13 illustrates a partial cross sectional view of a depletable unit II according to some embodiments of the present invention.

FIG. 13 is another embodiment of a well, showing a well 206 with an entry aperture 2063 and an exit aperture 2065. The well entry aperture 2063 is disposed adjacent the distal surface opposite an entry port 2003 provided in the envelope 2001. The entry port 2003 is blocked by an entry seal 2085, which may be either simply a portion of the envelope 2001, or be a viscoelastic seal embedded in the envelope as an insert. The entry seal 2085 may be manufactured by double-injection or by a similar production technique.

The well exit aperture 2065 is preferably disposed adjacent the proximal surface, opposite an exit port 2005 provided in the envelope 2001. It is through the exit aperture 2065 that air may be purged.

Figure 14:
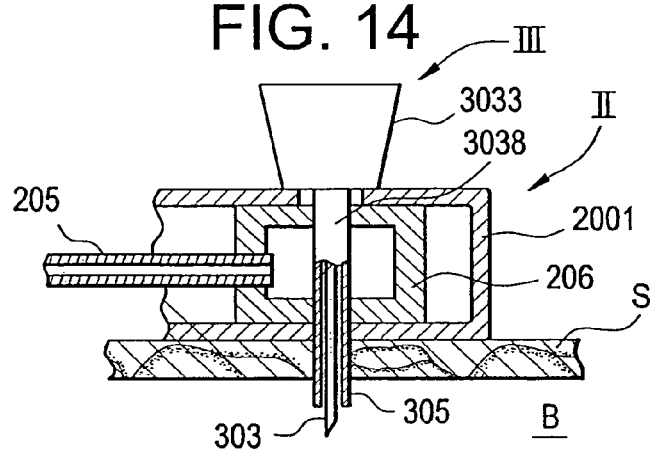
FIG. 14 illustrates a partial cross-sectional view of the depletable unit II shown in FIG. 13, having an injection unit III partially engaged therein according to some embodiments of the present invention.

FIG. 14 illustrates another embodiment of an injection unit III that has been inserted into the well 206 shown in FIG. 13.

The injection unit III may include a ram 3038 disposed intermediate the handle 3033 and the cannula 305, which is fitted with the trocar 303. One side of the ram 3038 may be fixedly attached to the handle 3033, and the opposite side of the ram, may be fixedly attached to the trocar 303. During insertion of the cannula 305 into the skin S or body B, by pushing on the handle 3033, the ram 3038 drives the cannula 305 until the handle 3033 is arrested by abutment on unit II. In that arrested position, which is depicted in FIG. 14, the cannula 305 is retained in place by friction at the well 206 and at unit II.

Figure 15:
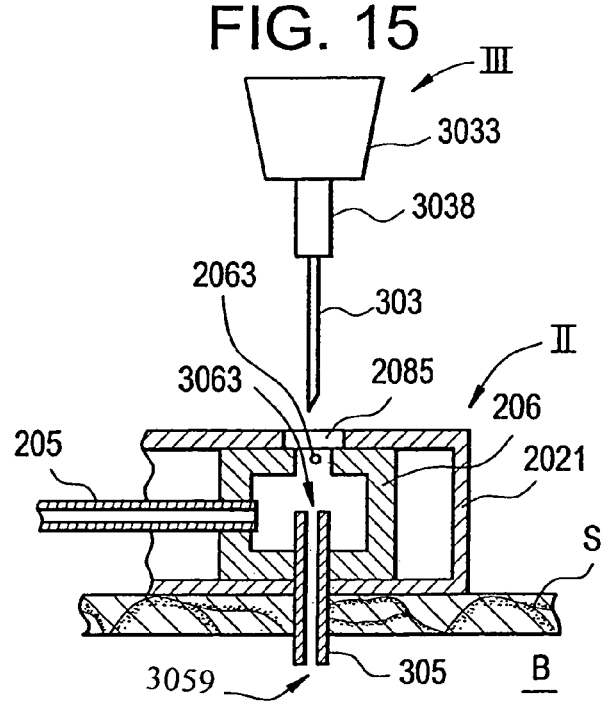
FIG. 15 illustrates a trocar of an injection unit III after retraction out of the depletable unit II of FIG. 13, according to some embodiments of the present invention.

FIG. 15 shows the trocar 303 after retraction out of the depletable unit II, and ready to be discarded. The cannula 305 is retained in the body B enabling liquid to flow out of the tube 205, into the well 206, and from there, into the cannula inlet opening 3063, via the cannula discharge opening 3059, and into the body.

The entry aperture 2063 and the exit aperture 2065 may be appropriately sealed to assure flow of liquid only via the cannula 305, and thus prevent unwanted escape and loss of liquid out of the well 206.

FIG. 16 shows a well 206 featuring a vent tube 2091 with a vent tube inlet 2093, and a vent tube outlet 2095, providing for fluid communication from the interior of the well 206 to the exterior of the envelope 2001. The vent tube 2091 may be inserted into the well 206 and the envelope 2001; the well and envelope may be made of viscoelastic material to prevent fluid exit but via the lumen of the vent tube 2091.

A cap may be included for covering the vent tube outlet 2095, but it is not shown in the figures, since it is removed prior to use. If desired, an entry seal 2085 may be appropriately disposed in the envelope 2001. As described hereinabove, air may be purged before or after coupling of the reusable unit I with the depletable unit II.

In FIG. 16, an embodiment of the injection unit III is the same as that of FIGS. 14 and 15. Upon insertion of the injection unit III into unit II, the trocar 303 and the cannula 305 pierce both the envelope 2001 and the well 206, and also pierce the entry seal 2085, if it is mounted. During insertion, the bottom portion 3037 of the handle 3033 pushes the vent tube 2091 into the well 206 and seals the vent tube outlet 2095. The cannula 305 is retained in position due to friction, as described hereinabove with reference to FIGS. 14 and 15.

FIG. 17 shows a cannula 305 driven by a cannula driver 3039 that is fixedly retained to the handle 3033 of the trocar 303. The cannula driver 3039 is affixed to the handle 3033 and to the trocar 303 instead of the ram 3038 shown in FIGS. 14, 15, and 16.

The cannula driver 3039 operates in association with a cannula 305 having a male screw thread 3058 disposed on the exterior portion adjacent the cannula inlet opening 3063. The cannula driver 3039 may be configured to engage the cannula inlet opening 3063 or a portion of the cannula adjacent thereto, to allow longitudinal insertion into the well 206, and rotation of the cannula. The trocar 303 is preferably linearly driven into the well 206 and then rotated to engage the screw thread 3058, either in self-tapping mode, or to engage a matching female screw thread appropriately provided, in the exit opening 2065.

Once the cannula 305 is firmly threaded and retained into the well 206, the trocar handle 3033 may be pulled out of the unit II, which may also retrieve the cannula driver 3039. The cannula inlet 3063 is now open to permit transfer of liquid from the well 206 to the skin S or body B.

In FIGS. 11, 12, and 14 to 17, the cannula 305 is shown for insertion in perpendicular direction into the skin S. However, if desired, other configurations may be possible which permit insertion of the cannula 305 at other desired angles.

FIG. 18 depicts still further embodiment of the dispenser, which is provided with a rotary joint 60 allowing rotation of the injection unit III in both clockwise and anticlockwise direction, for insertion of the cannula 305 at any angle from 0° to n 360°, with n ranging from 0 to ∞. In practice, insertion may be made at an angle ranging between the vertical and horizontal direction of the cannula relative to the skin S.

FIG. 18 is a partial cross-section of a plan view of unit II, showing the downstream extremity 2051 of the flexible tube 205 fixedly coupled in fluid communication with the entry aperture 2063 of the well 206. In FIG. 18, the well 206 is disposed in a horizontal position, being substantially parallel with the skin contacting surface of unit II.

The entry aperture 2063 preferably opens into a trap 2071 forming a cavity for liquid accumulation. The cavity is restricted by a step 2075 to form a cylindrical exit aperture 2065 of the well 206 that emerges onto a side wall or height surface of unit II. In contrast, with the well shown in FIGS. 10 to 17, the entry aperture 2063 is concealed and contained in the interior of unit II.

The rotary joint may be provided with a rotary fastener 61 coupled with the exit aperture 2065 of the well 206 An exterior portion 62 of the rotary fastener 61 supports an entry seal 2085 and a cannula 305, which is provided with a radial bore 69. The cannula is directed perpendicularly with respect to the well 206. The rotary fastener is provided with an internal channel, which provides fluid communication with the well and with the radial bore 69 of the cannula. The rotary fastener 61 includes an interior portion 63 terminating by resilient expandable jaws 65, and a cylindrical stem 66 intermediate the exterior portion 62 and the jaws 65.

The interior portion 63 of the rotary fastener 61 is preferably retained within the cylindrical exit aperture 2065. The resilient jaws 65 may be prevented from exiting out of the trap 2071 by virtue of the step 2075 and the stem 66 may be rotated in the cylindrical exit aperture 2065. An O-ring seal 64 intermediate the cylindrical exit aperture 2065 and the stem 66 prevents leakage of fluid.

The rotary fastener 61 may thus be free to rotate relative to the well 206 and the unit II. To prevent loose rotation or to retain the rotary fastener 61 in a desired position, a tongue 67 may be fixedly attached to the unit II for accommodating within grooves 68 cut on the periphery of the exterior portion 62 of the rotary fastener 61.

Before introduction of a "dagger" trocar 303 fitted with a handle 3033, and upon filling the reservoir 203 and purging out of air, the cannula 305 may serve for the exit of liquid. However, it is also possible to purge air when the cannula 305 is fitted with the trocar 303. To that end, the trocar 303 is hollow, and is provided with a radial bore 69 for liquid communication with the well 206 and with the exterior of unit II.

Figure 19:
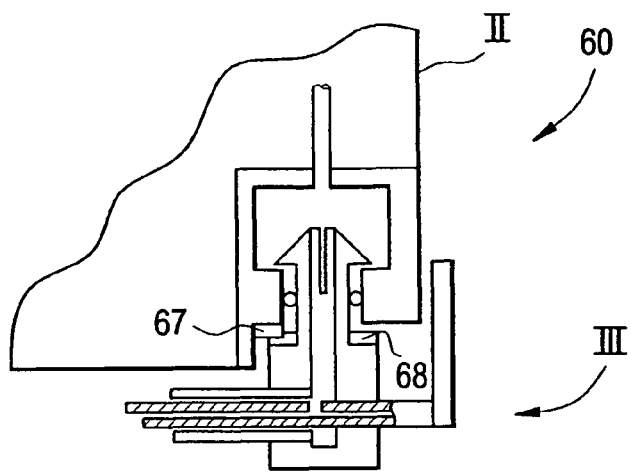
FIG. 19 illustrates a partial cross sectional plan view of a depletable unit II according to some embodiments of the present invention.

In FIG. 18, the cannula 305 is received within the fastener 61 and is situated inside a cutout 71 provided in the unit II. A different embodiment of the rotary joint is shown in FIG. 19, in which the unit II is not provided with the cutout 71. The tongue 67 and the grooves 68 may be disposed slightly differently.

In both embodiments shown in FIGS. 18 and 19, the unit III may be configured differently. In FIG. 18, unit III may include a dagger trocar 303 fitted with a handle 3033, or including a hollow trocar 303 with a handle 3033. Unit III may take advantage of any of the embodiments depicted in the FIGS. 11 to 17.

In yet another embodiment, the unit III includes rotary fastener 61 with the trocar 303 and the cannula 305 already inserted therein. In that case, the well 206 may be fitted with an exit plug 2069, which may be removed for air purging.

Figure 20:
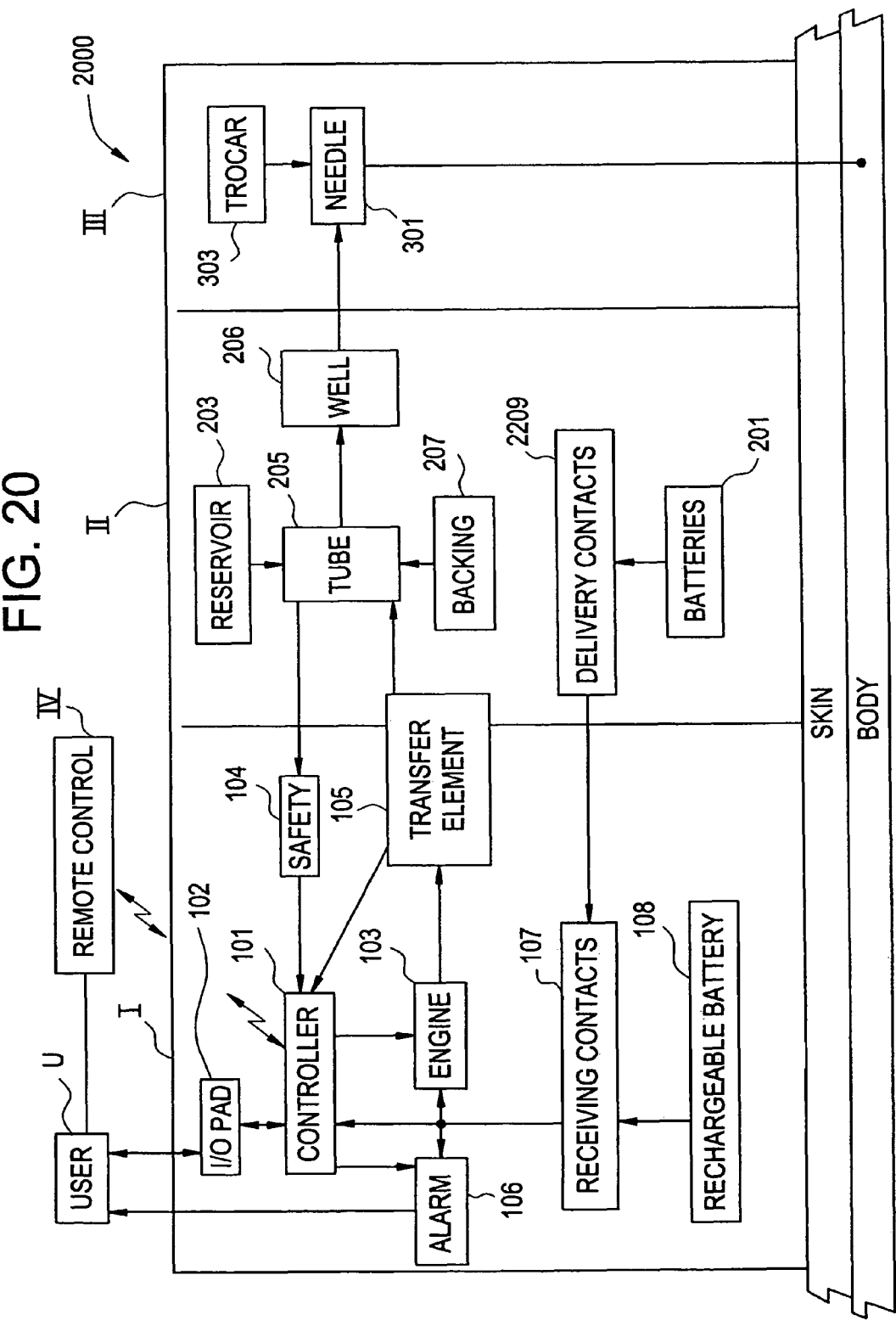
FIG. 20 illustrates a block diagram of a fluid delivery system according to some embodiments of the present invention.

FIG. 20 shows optional components for integration with the reusable unit I, as embodiment 2000. Such options may include an Input/Output pad (or I/O pad) 102, a safety device 104, an alarm 106, and one or more rechargeable batteries 108.

It is possible to add an I/O device on the distal exterior face of the reusable unit I, opposite that face of the unit, which adheres to the skin S. Thereby there is provided an additional means for communication. The I/O pad 102 may be fitted with input means such as button(s) and/or keys, or a USB port, and output means such as LEDs, and even with a display if desired. The I/O pad 102 is coupled to, and receives input and output commands from both, the controller and transceiver 101, and from the user U.

A safety device 104 may be coupled to an independent flow sensor configured to monitor the fluid pressure pulses delivered to the downstream extremity 2051 of the flexible tube 205.

In contrast with the controller and transceiver 101, which derives the flow rate, i.e. volume/time of liquid transferred to the body B, as by equation (1) hereinabove, the safety device 104 may directly sense pulses of liquid pressure generated in the tube 205. The addition of a stand-alone fluid flow sensor, not shown in the figures, may be added if desired, to enhance the reliability of the system 1000.

Figure 21:
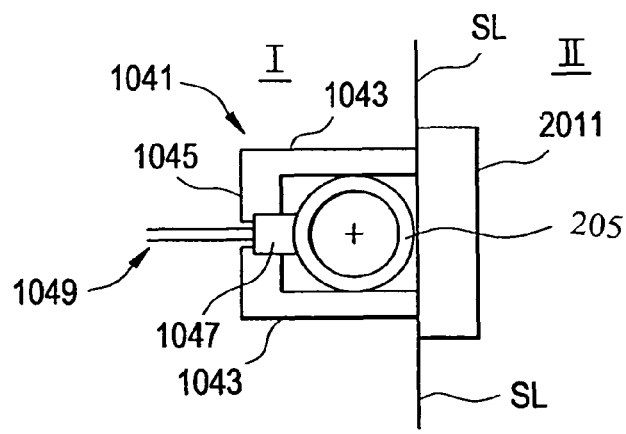
FIG. 21 is a schematic diagram of a pressure sensor device according to some embodiments of the present invention.

FIG. 21 is a schematic presentation of an exemplary pressure sensor device. The tube 205 is seen in cross-section, supported by a rigid base 2011 carried by the depletable unit II, while a rigid bridge 1041 disposed on the reusable unit I, embraces the tube 205.

The bridge 1041 may include one or more legs, and preferably, two legs 1043, distanced and separated apart, both legs may be supported on the base 2011, and one beam 1045 supported by the two legs 1043. The separation line SL in FIG. 21 indicates a border between unit I and unit II, and thus marks the separation line between the bridge 1041 and the base 2011. When both units I and II are coupled together for operation, the tube 205 is tightly encaged in a rigid frame formed by the bridge 1041 and the base 2011.

A piezoelectric pressure sensor 1047, as an example of a pressure sensor device, may be retained in the beam 1045 disposed opposite the base 2011 to be in direct mechanical contact with the tube 205. When a pulse of liquid surges in the interior of the tube 205, the piezoelectric pressure sensor 1047 senses that pulse, which is translated into an electrical signal communicated via a couple of leads 1049 to the controller and transceiver 101.

Figure 22:
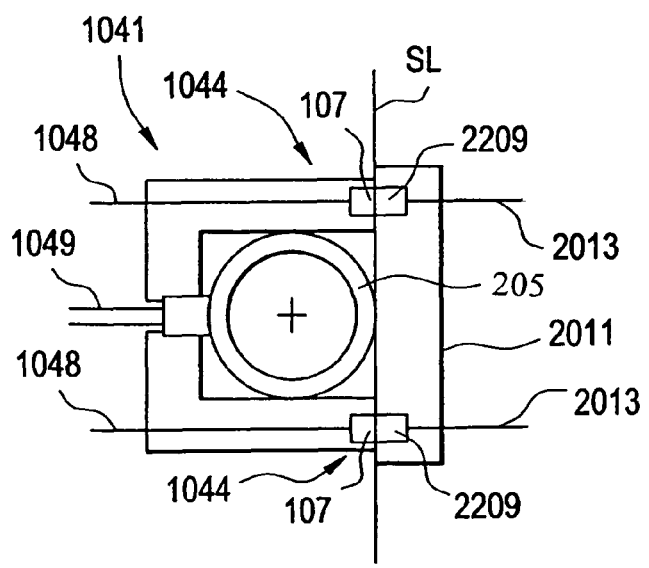
FIG. 22 is a schematic diagram of the integration of delivery and receiving contacts into structure of a pressure sensing device according to some embodiments of the present invention.

FIG. 22 shows schematically an advantage taken from the disposition of the two legs 1043 to integrate both the delivery and receiving contacts, respectively 2209 and 107, into the structure of the pressure sensor device 1047.

A receiving contact 107 may be disposed in the free extremity 1044 of each leg 1043, and a delivery contact 2209 may be disposed opposite thereto on the base 2011. A lead 1048 may be electrically coupled to each receiving contact 107 passing in the interior of each leg 1043.

A lead 2013 may be electrically coupled to each delivery contact 2209 passing through the base 2011. Although not shown in the figures, each one or both contacts out of a pair comprising a delivery contact 2209 and a receiving contact 107 may be spring-loaded for better conductance, if desired.

The piezoelectric pressure sensor 1047, which responds by emitting signals in proportion to trains of quanta of fluid 1055 flowing through the tube 205, may easily detect basal and bolus fluid flow patterns, and report accordingly to the controller and transceiver 101. Furthermore, high pressure, such as caused by an occlusion, or low pressure, such as caused by a leak, e.g. disengagement or rupture, will also easily be detected and reported.

In a train of pressure pulses, each pulse may be characterized by an amplitude A, by a pulse width w, and by a distance T separating two consecutive pulses, indicative of the period T.

Figure 23:
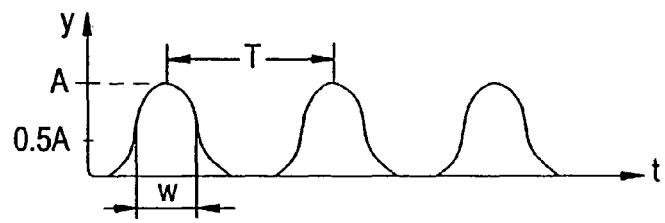
FIG. 23 is a graph of a pulse train derived by piezo-electric pressure sensor according to some embodiments of the present invention.

FIG. 23 shows a graph as an example of a pulse train derived by the piezoelectric pressure sensor 1047, with respect to a set of coordinates having an abscissa t, indicating time, and an ordinate y designating amplitude. The pressure pulse waveform contains information regarding the operational status of the system 1000, say as represented by the three parameters A, w, and T.

The amplitude A may be proportional to the pressure of the liquid in the tube 205, and preferably remains within predetermined boundaries. Too high an amplitude A, thus too high a pressure, may indicate an occlusion. On the contrary, low pressure may point to a leak, such as a rupture, release, disconnection, or even lack of liquid.

In one embodiment, the period T may be proportional to the speed of rotation of the wheel 1051 of the transfer element 105, thus proportional to the volume of injected quanta of liquid. In FIG. 23, the surface delimited between the curve of the measured pressure wave and the abscissa t, thus comparative to the multiplication of A and w divided by T, is indicative of the flow rate Q of the injected liquid, as represented by equation (2):

$$Q=k*A*w/T \text{ [mm}^3\text{/min]} \qquad (2)$$

The coefficient k is an empirical one-dimensional coefficient, and depends on the interior diameter of the tube 205.

The safety device 104 is a valuable independent support tool enhancing the reliability of the system 1000 regarding the delivery of alarm in case a trend pointing to a developing dangerous situation or to an imminent danger is detected in some embodiments of the invention.

Although not shown in the figures, one or more safety devices 104 may be added, such as a flow sensor, in replacement of, or in addition to the pressure sensor 1047.

An alarm module 106 may be provided, which may be coupled to the receiving contacts 107 providing power, and to the controller and transceiver 101. The alarm module 106 may be used to provide alert in response to a danger signal emitted by the controller and transceiver 101, and/or by the safety device 104. The alarm module 106 may be implemented to emit an audible, visual, or sensory signal, by operation of, respectively, a buzzer, a light, or a vibrator. The vibrator is the preferred implementation since unit I is disposed on the skin S, and it is also preferred because the delivered signal is a privately sensed one, without the surroundings being aware thereof.

An alarm may be given in response to a signal from the controller and transceiver 101, according to at least one of the following: a detected unacceptable condition and performance of the engine 103, a signal from the reusable sensor 21, or a signal from the safety device 104. The safety device 104 may be coupled to the alarm module 106 via the controller and transceiver 101, or directly thereto, even though such a connection is not shown in the figures.

The engine 103, the safety device 104, and the transfer element 105 are activated only after operative connection of the reusable unit I with the depletable unit II is established. In parallel, the controller and transceiver 101 may emit wireless alarm signals to the remote control unit IV, which may relay those alarm signals to other external receiving devices, computers, and networks.

Optionally, a battery, possibly a rechargeable battery 108, is also integrated within the reusable unit I, to provide additional reliability to the system 1000. The battery 108 may be charged by connection to an external battery charger via a charging port.

In FIG. 20 the controller and transceiver 101 are shown coupled to the I/O pad 102, the engine 103, the safety device 104, the transfer element 105, the alarm 106, and in bi-directional wireless communication with the remote control unit IV. The controller and transceiver 101 may be microprocessor-driven for commanding and managing units I and II, and configured to support bi-directional wire and wireless communication with the remote control unit IV.

Figure 24:
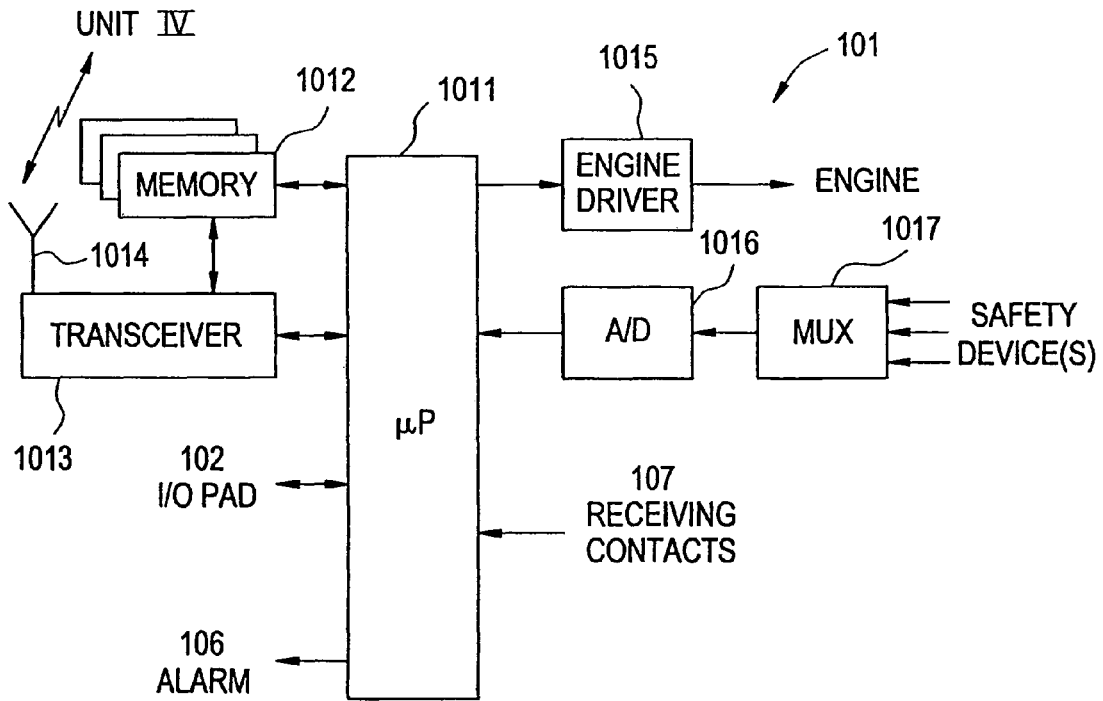
FIG. 24 is a block diagram of an electronic circuit for a reusable unit according to some embodiments of the present invention.

FIG. 24 illustrates an exemplary block diagram presenting the electronic circuit of the controller and transceiver 101, which is a control-with-transceiver module. A microprocessor (or μP) 1011, having one or more memories 1012, is coupled to a transceiver 1013 having an antenna 1014. The μP 1011 may also be coupled to an engine driver 1015, an A/D converter 1016, which in turn, is coupled to a MUX 1017. The μP 1011 may be configured to read, operate and run computer programs stored in the one or more memories 1012, referred to hereinbelow as the memory 1012, as well as to respond to instructions and commands.

For example, the μP 1011 receives commands from the remote control unit IV via the antenna 1014 and the transceiver 1013, then fetches data and computer programs from the memory 1012, and stores data therein. The transceiver 1013 also preferably communicates with the memory 1012 to store programs and data therein and to retrieve data therefrom. It is via the antenna 1014 that the transceiver 1013 communicates with the remote control IV, and if desired, with other receivers, emitters or transceivers, not shown in the figures.

The μP 1011 may then emit commands to the engine driver 1015 for activation of the engine 103, and receive feedback from one or more safety device(s) 104. From the received feedback, the μP 1011 may derive comparisons, and may, if necessary, emit correction commands to the engine driver 1015.

Feedback signals from the safety device(s) 104, received from analog sensors, may be fed to the μP 1011 via a MUX 1017, and converted by an A/D converter 1016 into digital signals.

Furthermore, data and commands may be exchanged between the μP 1011 and the I/O pad 102. The μR 1011 may also activate the alarm 106 when necessary. Power for running the μP 1011 may be obtained from the receiving contacts 107 coupled to batteries mounted in unit II, or to an optional battery 108, rechargeable or not, mounted on unit I.

In practice, the electronic circuit of the controller and transceiver 101 may be integrated in a manner well known to the art, as a low power-consuming single chip, such as an ASIC, e.g. Chipcon®, Zarlink®, and the like.

Figure 25:
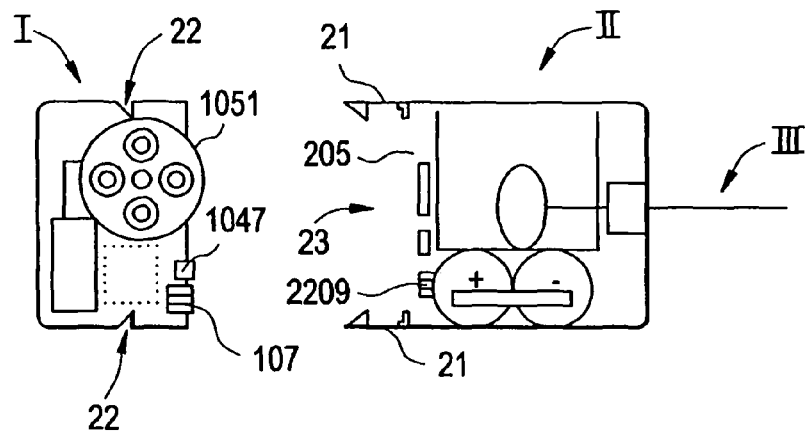
FIG. 25 is a schematic diagram of a reusable unit I and a depletable unit II, separated, according to some embodiments of the present invention.

FIG. 25 shows unit I and unit II separated from each other, while unit III is depicted symbolically as being coupled to unit II, even though shown in the plane of the paper instead of being in perpendicular thereto. Unit II may include releasable latching arms 21 and a recess 23 to receive unit I. Unit I may include latching grooves 22 configured to engage the latching arms 21, to firmly but releasably retain both units I and II together.

Figure 26:
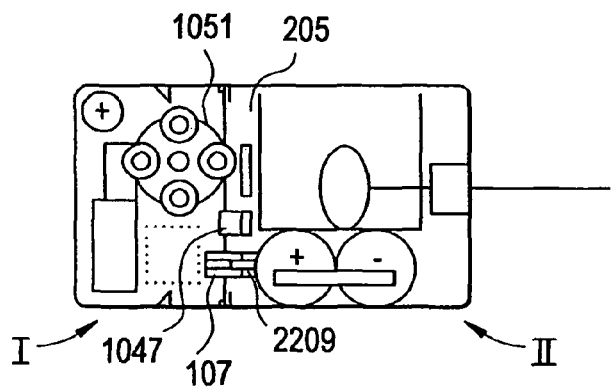
FIG. 26 is a schematic diagram of the reusable unit I and the depletable unit II, connected, according to some embodiments of the present invention.

In some embodiments, when both units I and II are latched together, as shown in FIG. 26, both the wheel 1051 and the sensor 1047 appropriately abut the tube 205, and likewise, the delivery contacts 2209 engage the receiving contacts 107.

Figure 27:
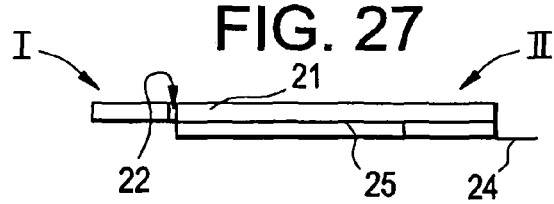
FIG. 27 is a side view of an assembled reusable unit I and depletable unit II, positioned next to the skin of a patient, according to some embodiments of the present invention.

FIG. 27 is a side elevation of the latched units I and II. A strip of peel-off tape 24 covers a layer of adhesive 25. With the tape 24 taken off, the unit II may be brought in contact with the skin S, not shown in FIG. 27, to adhere thereto. If desired, but not shown in FIG. 27, adhesive may be added to unit I in the same fashion as described for unit II.

Figure 28:
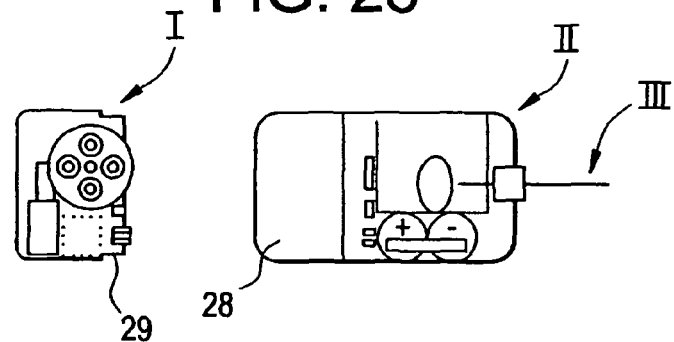
FIG. 28 is a schematic diagram of a reusable unit I and depletable unit II, separated, with injection unit III depicted symbolically (coupled to unit II in the plane of the figure), according to some embodiments of the present invention.

FIG. 28 presents another embodiment, which also shows unit I and unit II separated from each other, while unit III is again depicted symbolically as being coupled to unit II in the plane of the paper instead of being in perpendicular thereto. Unit II is shown to have a cradle 28 for releasably receiving unit I therein.

Figure 29:
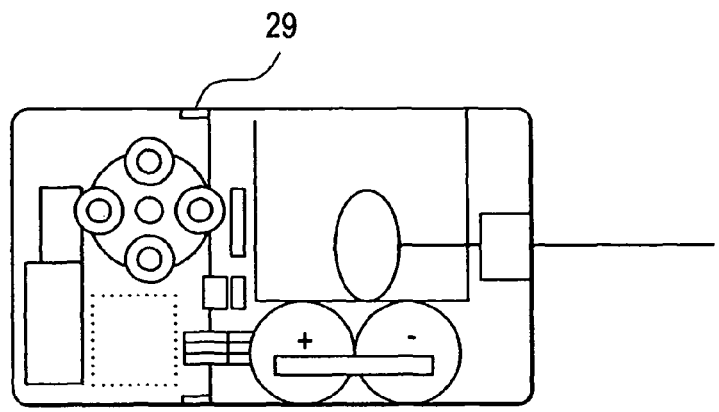
FIG. 29 is a schematic diagram of the reusable unit I and the depletable unit II shown in FIG. 28, connected.

FIG. 29 depicts unit I securely snapped into the cradle 28, but releasable therefrom when depleted. In the same manner, as for unit II in FIG. 27, the bottom of unit I may also be covered with peel-off tape 24 covering a layer of adhesive. An O-ring 29, or other sealing element 29, may be coupled to unit I to ensure sealing when engaged with unit II.

One of skill in the art will appreciate that other releasable snap-on mechanisms are also available to firmly couple both units I and II when engaged.

Figure 30:
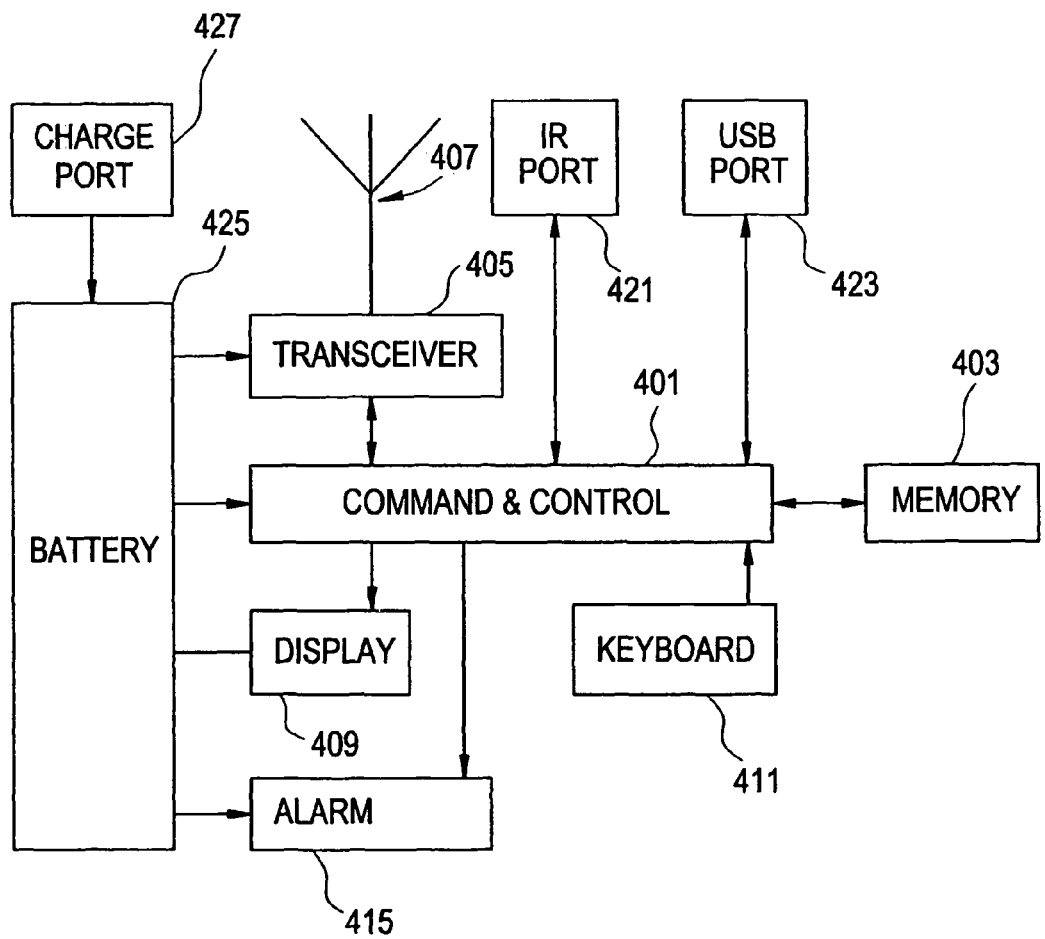
FIG. 30 is a block schematic diagram of a remote control unit IV according to some embodiments of the present invention.

FIG. 30 is a block diagram of an example of the remote control unit IV, which is a handheld set operated by the user U. In some embodiments, the remote control unit IV is the user interface with the system 1000, by which programs and/or commands are emitted and received, and the system 1000 is operated and controlled.

As shown, microprocessor-driven command and control unit 401, which is able to run computer programs stored in a memory 403, is coupled to a transceiver 405, which in turn is coupled to an antenna 407, for wireless bi-directional communication with at least unit I. Communication with external devices, computers, and networks is also possible, if desired. The command and control unit 401 may also be coupled to a display 409, and to an alphanumeric keyboard 411. An alarm device 415, such as a LED, a buzzer, or other known devices, may further be coupled to the command and control unit 401.

Exchange of information, such as computer programs, memory data, instructions, and commands is achieved with the system 1000 (for example), and with other external and remote devices, computers, and networks, not only via the transceiver 405, but also via an Infra Red port (or IR port) 421, and a USB port 423.

Power for operation of the remote control unit IV may be supplied by a battery 425, which is replaceable, or reloaded via a battery charge port 427. The battery may power the command and control unit 401, the transceiver 405, the display 409, and the alarm device 415. It is noted that the battery 425, the memory 403, the USB port 423, and the alarm 415, shown as single devices in FIG. 30, may be implemented as multiple devices if desired.

For operation, the memory 403 of the remote control unit IV may be loaded with programs via the transceiver 405, or via the IR port 421, or via the USB port 423. For injection of the liquid, according to needs, the user U may enter instructions and commands via the keyboard 411, to communicate via the transceiver 405 and the antenna 407, with the controller and transceiver 101 of the reusable unit I.

Information received from sources external to the units of the system 1000, as well as data received from unit I, may be displayed on the display 409. The command and control unit 401 may analyze system status and receive data for output of selected information and necessary alarms on, respectively, the display 409 and the alarm 415. The display 409 may also be able to show various status data, such as liquid delivery rate, computer program actually running, and battery state.

The exchanges of data and the communication processes may be governed by known techniques ensuring data security and data integrity, and taking advantage of known handshaking and secured communication protocols, all well known to the art.

A handset I/O pad can be disposed on the remote control unit IV, having the display 409, the keyboard 411, and the alarm 415.

Operation of the system 1000 is described hereinbelow by way of example only, since the order of operations performed may vary.

Prior to use (and preferably upon manufacture), general programs, instructions and commands may be preloaded into the remote control IV, and thereafter, personalized data for the individual user U may be added.

For treatment, the user U selects a liquid to be injected, such as insulin for example, and further chooses a desired type of unit II. If the reservoir 203 in unit II is not supplied pre-filled, the user U may manually fill the reservoir 203, taking care of purging air therefrom. Then, unit II with the reservoir 203 is operatively coupled to the reusable unit I. The user U now selects a type of unit III, as desired, or as needed. In turn, unit III is inserted into unit II to establish fluid communication therewith, whereafter the user U commands operation of the transfer element 105 to purge air out of the cannula 305. Next, unit III is operated for insertion of the cannula 305 into the skin S or subcutaneously into the body B, and the operationally assembled units I, II, and III are appropriately disposed for at least unit II to adhere to the skin.

When unit II is coupled to unit I, power is supplied to unit I from the single or multiple batteries, via the delivery contacts 2209 and the receiving contacts 107. The controller and transceiver 101 may execute computer programs and instructions as commanded by the user U, via unit IV, or via the I/O pad 102. Computer programs and instructions may also be deliverable to the controller and transceiver 101 as captured from an external source. Emissions from external sources may be captured by unit IV through the wireless transceiver 405, via the antenna 407, or the IR port 421, or by wire via the USB port 423. Such external transmissions may be received from devices external to the system 1000, from remote computers or networks.

Upon command, liquid is dispensed from the reservoir 203 according to computer programs stored in memory, or in response to command from the user U. Then, the engine 103 activates the transfer element 105 in associative operation with the tube 205 and the backing 207, to fill the well 206. Unit III forwards liquid from the well 206 and into the skin S or subcutaneously into the body B.

Faultless operation of the system 1000 may be monitored by the controller and transceiver 101, and to enhance reliability, also supported by feedback signals received from a reusable sensor 21 disposed on the transfer element 105, and/or from the safety device 104 coupled to disposable sensors disposed on unit II.

To further enhance reliability of the system 1000, at least one rechargeable battery may be disposed in unit I.

The system 1000 is thus an example of a sustained release delivery system for delivering a beneficial liquid at a predetermined rate to the skin S or body B.

Having now described some embodiments of the invention, it should be apparent to those skilled in the art that the foregoing is merely illustrative and not limiting, and it should be understood that numerous changes in such embodiments may be introduced without departing from the true spirit of the invention as defined in the appended claims.

What is claimed is:

1. A medical device for delivering therapeutic fluid to a body of a patient, the device comprising:
a reusable unit comprising:
a controller, and
a first portion of a fluid transfer system;
a disposable unit comprising:
a reservoir for holding the therapeutic fluid,
a second portion of the fluid transfer system,
an exit port, and
a cradle for releasably receiving the reusable unit; and
a cannula unit comprising:
a cannula for insertion into the body of the patient, and
a penetrating needle fitted to the cannula and configured to be removed from the cannula after insertion of the cannula into the body;
wherein:
upon coupling the reusable unit and the disposable unit, the first portion of the fluid transfer system operatively couples to the second portion of the fluid transfer system, enabling transfer of the therapeutic fluid from the reservoir to the exit port, and
upon coupling the cannula unit and the disposable unit, and insertion of the cannula into the body of the patient, fluid communication is established from the exit port to the body, via the cannula, without the use of tubing external to the coupled reusable and disposable units.

2. The device according to claim 1, wherein the fluid transfer system comprises a pump.

3. The device according to claim 1, wherein:
the disposable unit further comprises a tube configured, to transfer the therapeutic fluid from the reservoir to the exit port, and
the tube is substantially contained within the disposable unit.

4. The device according to claim 1, wherein at least the disposable unit is releasably adherable to the skin of the patient.

5. The device according to claim 1, wherein the cannula unit is configured for insertion through the disposable unit to establish fluid communication therebetween.

6. The device according to claim 1, wherein the cannula is configured for insertion into the body at any desired angle.

7. The device according to claim 1, further comprising at least one source of energy.

8. The device according to claim 7, wherein the at least one source of energy is located in the disposable unit.

9. The device according to claim 8, wherein:
the disposable unit includes delivery contacts electrically connected to the at least one source of energy,
the reusable unit includes receiving contacts, and
upon operative coupling of the reusable unit and the disposable unit, the delivery contacts are coupled to the receiving contacts to delivery power to the reusable unit.

10. The device according to claim 1, further comprising a flow sensor.

11. The device according to claim 1, wherein the reusable unit further comprises an alarm.

12. The device according to claim 1, wherein the reusable unit further comprises a rechargeable battery.

13. The device according to claim 1, wherein the reusable unit includes an I/O pad.

14. The device according to claim 1, further comprising a sealing element coupled to the reusable unit to ensure sealing when the reusable unit is coupled with the disposable unit.

15. The device according to claim 1, wherein the therapeutic fluid comprises insulin.

16. A medical system for delivering therapeutic fluid to a body of a patient, the system comprising:
the device according to claim 1; and
a remote control unit.

17. The system according to claim 16, wherein the communication between the reusable unit and the remote control unit is wireless.

18. The system according to claim 16, wherein at least one of the reusable unit and the remote control unit includes a USB port.

19. A medical device for delivering therapeutic fluid to a body of a patient, the device comprising:
a reusable unit comprising:
a controller, and
a first portion of a fluid transfer system;
a disposable unit comprising:
a reservoir for holding the therapeutic fluid,
a second portion of the fluid transfer system,
a well configured for use with a cannula for inserting into the body through the well and coupling thereto to provide fluid communication between the disposable unit and the body; and
a cannula unit configured for insertion into the disposable unit at the well, the cannula unit comprising:
a cannula for insertion into the body of the patient through the well, and
a penetrating needle fitted to the cannula and configured to be removed from the cannula after insertion of the cannula into the body;
wherein:
upon coupling the reusable unit and the disposable unit, the first portion of the fluid transfer system operatively couples to the second portion of the fluid transfer system, enabling delivery of the therapeutic fluid from the reservoir, and
upon insertion of the cannula unit into the disposable unit at the well and insertion of the cannula into the body of the patient through the well, fluid communication is established from the disposable unit to the body, via the cannula, without the use of tubing external to the coupled reusable and disposable units.

20. A medical device for delivering therapeutic fluid to a body of a patient, the device comprising:
a reusable unit comprising:
a controller, and
a first portion of a fluid transfer system;
a disposable unit comprising:
a reservoir for holding the therapeutic fluid,
a second portion of the fluid transfer system,
a well configured for use with a cannula for inserting into the body through the well and coupling thereto to provide fluid communication between the disposable unit and the body; and
a cannula unit configured for insertion into the disposable unit at the well, the cannula unit comprising:
a cannula for insertion into the body of the patient through the well, and
a penetrating needle fitted to the cannula and configured to be removed from the cannula after insertion of the cannula into the body;
wherein:
upon coupling the reusable unit and the disposable unit, the first portion of the fluid transfer system operatively couples to the second portion of the fluid transfer system, enabling delivery of the therapeutic fluid from the reservoir, and upon insertion of the cannula unit into the disposable unit and insertion of the cannula into the body of the patient through the well, the cannula is arranged immediately adjacent coupled reusable and disposable units and projects away from a side or bottom of the coupled reusable and disposable units.

21. A medical device for delivering therapeutic fluid to a body of a patient, the device comprising:
  a reusable unit comprising:
    a controller, and
    a first portion of a fluid transfer system;
  a disposable unit comprising:
    a reservoir for holding the therapeutic fluid,
    a second portion of the fluid transfer system,
    an exit port, and
    a cradle for releasably receiving the reusable unit; and
  a cannula unit comprising:
    a cannula for insertion into the body of the patient, and
    a penetrating needle fitted to the cannula and configured to be removed from the cannula after insertion of the cannula into the body;
  wherein:
    upon coupling the reusable unit and the disposable unit, the first portion of the fluid transfer system operatively couples to the second portion of the fluid transfer system, enabling transfer of the therapeutic fluid from the reservoir to the exit port, and
    upon coupling the cannula unit and the disposable unit, and insertion of the cannula into the body of the patient, the cannula is arranged immediately adjacent coupled reusable and disposable units and projects away from a side or bottom of the coupled reusable and disposable units.

* * * * *